US009187754B2

(12) United States Patent
Boonchird et al.

(10) Patent No.: US 9,187,754 B2
(45) Date of Patent: Nov. 17, 2015

(54) **MODIFIED *BORDETELLA PERTUSSIS* STRAINS**

(71) Applicant: BIONET-ASIA, CO. LTD., Bangkok (TH)

(72) Inventors: Chuenchit Boonchird, Bangkok (TH); Wasin Buasri, Bangkok (TH); Watanalai Panbangred, Bangkok (TH); Jean Petre, Wavre (BE)

(73) Assignee: BIONET-ASIA, CO. LTD., Bangkok (TH)

( * ) Notice: Subject to any disclaimer, the term of this patent is extended or adjusted under 35 U.S.C. 154(b) by 0 days.

(21) Appl. No.: 14/309,807

(22) Filed: Jun. 19, 2014

(65) Prior Publication Data

US 2014/0302558 A1     Oct. 9, 2014

Related U.S. Application Data

(63) Continuation of application No. PCT/TH2012/000052, filed on Dec. 20, 2012.

(30) Foreign Application Priority Data

Dec. 21, 2011   (ZA) ................................. 2011/09417

(51) Int. Cl.
| | |
|---|---|
| *C12N 1/20* | (2006.01) |
| *C12N 15/09* | (2006.01) |
| *C12N 15/74* | (2006.01) |
| *C12P 21/06* | (2006.01) |
| *C12P 21/04* | (2006.01) |
| *C12N 15/64* | (2006.01) |
| *A01N 63/00* | (2006.01) |
| *A61K 48/00* | (2006.01) |
| *A61K 39/00* | (2006.01) |
| *A61K 38/00* | (2006.01) |
| *C07K 14/235* | (2006.01) |
| *C12P 21/00* | (2006.01) |
| *C12N 15/70* | (2006.01) |
| *C12N 15/86* | (2006.01) |

(52) U.S. Cl.
CPC ............... *C12N 15/74* (2013.01); *A61K 38/00* (2013.01); *C07K 14/235* (2013.01); *C12P 21/00* (2013.01); *C12N 15/70* (2013.01); *C12N 15/86* (2013.01)

(58) Field of Classification Search
CPC .. C07K 14/235; C07K 14/005; A61K 39/099; A61K 2039/53; C12N 7/00
See application file for complete search history.

(56) References Cited

U.S. PATENT DOCUMENTS

| | | | |
|---|---|---|---|
| 5,085,862 A | 2/1992 | Klein et al. | |
| 5,221,618 A | 6/1993 | Klein et al. | |
| 5,244,657 A | 9/1993 | Klein et al. | |
| 5,358,868 A | 10/1994 | Klein et al. | |
| 5,433,945 A | 7/1995 | Klein et al. | |
| 5,439,810 A | 8/1995 | Loosmore et al. | |
| 5,786,189 A * | 7/1998 | Locht et al. | ................. 424/200.1 |
| 7,427,404 B1 * | 9/2008 | Pizza et al. | ................. 424/240.1 |
| 7,666,436 B1 | 2/2010 | Pizza et al. | |
| 2005/0026866 A1 * | 2/2005 | Pawelek | .......................... 514/54 |

FOREIGN PATENT DOCUMENTS

| | | | |
|---|---|---|---|
| JP | WO 2005/090576 A1 | * | 9/2005 |
| WO | WO 95/09649 | * | 4/1995 |

OTHER PUBLICATIONS

WO 2005/090576 A1—machine translation.*
Rappuoli et al., Vaccine, 1992; 10(14):1027-32.*
Stibitz S: Use of conditionally counterselectable suicide vectors for allelic exchange. Methods Enzymol 1994, 235:458-465.
Nencioni L, et al.: Characterization of genetically inactivated pertussis toxin mutants: candidates for a new vaccine against whooping cough. Infect Immun 1990, 58:1308-1315.
Sato, Y. and Sato, H. "Development of acellular pertussis vaccines," Biologicals, 1999, vol. 27, No. 2, pp. 61-69.
Pizza, M. et al., "Mutants of pertussis toxin suitable for vaccine development", Science 1989, vol. 246, No. 4929, pp. 497-500.
Loosmore, S.M. et al., "Engineering of genetically detoxified pertussis toxin analogs for development of a recombinant whooping cough vaccine", Infect. Immun., 1990, vol. 58, No. 11, pp. 3653-3662.
Barry, E.M., et al. "Expression and immunogenicity of pertussis toxin S1 subunit tetanus toxin fragment C fusions in *Salmonella typhi* vaccine strain CVD 908," Infect. Immun., 1996, vol. 64, No. 10, pp. 4172-4818.
Inatsuka, C.S. et al., "Pertactin is required for *Bordetella* species to resist neutrophil-mediated clearance," Infect. immun., 2010, vol. 78, No. 7, pp. 2901-2909.
Buasri, W. et al. "Construction of Bordetella pertussis strains with enhanced production of genetically-inactivated pertussis Toxin and Pertactin by unmarked allelic exchange," BMC Microbiol., Apr. 2012, vol. 12, No. 61, pp. 1-16.
International Search Report dated Jun. 11, 2013 for PCT/TH1012/000052.

* cited by examiner

*Primary Examiner* — Gary Nickol
*Assistant Examiner* — Lakia Tongue
(74) *Attorney, Agent, or Firm* — Knobbe, Martens, Olson & Bear, LLP

(57) ABSTRACT

Recombinant *Bordetella pertussis* strains derived from parent strain Tohama are provided. The new strains are obtained by homologous recombination using a allelic exchange vector pSS4245, which allows the replacement of sections of the bacterial chromosome without leaving any accessory mutations. The segment encoding PT subunit S1 is replaced to introduce two mutations causing inactivation of the toxic activity of PT. This strain can be further modified to express increased amounts of rPT and/or PRN. A second copy of the ptx cluster of the five PT structural genes of the ptx-ptl operon with their promoter and the ptl terminator and containing the above mutations can be inserted elsewhere on the chromosome. In addition, a second copy of the PRN gene can be inserted on the chromosome. In both cases, abandoned gene loci are selected as the insertion site to avoid the introduction of unwanted genetic alterations.

18 Claims, 7 Drawing Sheets

A. pSK5Cm3

B. pSK5S13-9K-129G

A. stage I: replacement of S1 gene by a $Cm^R$ gene

B. Stage II. Replacement of $Cm^R$ gene by the mutated S1 gene

Fig. 3

A. Selected insertion site

B. pSKPD5Cm3

C. pSKptxter with S1* (9K-129G)

A. Selected insertion site

B. pSKPD25FpPRN3

C. pSKPD25PRN3

SEQUENCE LISTING

<160> NUMBER OF SEQ ID NOS: 48

<210> SEQ ID NO 1
<211> LENGTH: 30
<212> TYPE: DNA
<213> ORGANISM: Artificial Sequence
<220> FEATURE:
<223> OTHER INFORMATION: 5'F-PT-SalI

```
<400> SEQUENCE: 1
gcggtcgacg gcgcgcaatg cggcgcggac                              30

<210> SEQ ID NO 2
<211> LENGTH: 57
<212> TYPE: DNA
<213> ORGANISM: Artificial Sequence
<220> FEATURE:
<223> OTHER INFORMATION: 5'R-PT-MCS

<400> SEQUENCE: 2
gggggcggcc gcgagatctc tctagacggt accatcgcgc gactttgcgc cgaagga    57

<210> SEQ ID NO 3
<211> LENGTH: 30
<212> TYPE: DNA
<213> ORGANISM: Artificial Sequence
<220> FEATURE:
<223> OTHER INFORMATION: 3'F-PT-XbaI

<400> SEQUENCE: 3
cgttctagac ctggcccagc ccgcccaac                               30

<210> SEQ ID NO 4
<211> LENGTH: 30
<212> TYPE: DNA
<213> ORGANISM: Artificial Sequence
<220> FEATURE:
<223> OTHER INFORMATION: 3'R-PT-BglII

<400> SEQUENCE: 4
ggcagatctg cagttcgagc agatcgccgg                              30

<210> SEQ ID NO 5
<211> LENGTH: 30
<212> TYPE: DNA
<213> ORGANISM: Artificial Sequence
<220> FEATURE:
<223> OTHER INFORMATION: CmF-KpnI

<400> SEQUENCE: 5
cgcggtacct gatgtccggc ggtgcttttg                              30

<210> SEQ ID NO 6
<211> LENGTH: 30
<212> TYPE: DNA
<213> ORGANISM: Artificial Sequence
<220> FEATURE:
<223> OTHER INFORMATION: CmR-XbaI

<400> SEQUENCE: 6
aatctagata tcgtcaatta ttacctccac                              30

<210> SEQ ID NO 7
<211> LENGTH: 30
<212> TYPE: DNA
<213> ORGANISM: Artificial Sequence
<220> FEATURE:
<223> OTHER INFORMATION: S1F-PT-KpnI

<400> SEQUENCE: 7
gatggtaccg gtcaccgtcc ggaccgtgct                              30

<210> SEQ ID NO 8
<211> LENGTH: 30
```

```
<212> TYPE: DNA
<213> ORGANISM: Artificial Sequence
<220> FEATURE:
<223> OTHER INFORMATION: S1R-PT-XbaI

<400> SEQUENCE: 8
caggtctaga acgaatacgc gatgctttcg                                      30

<210> SEQ ID NO 9
<211> LENGTH: 31
<212> TYPE: DNA
<213> ORGANISM: Artificial Sequence
<220> FEATURE:
<223> OTHER INFORMATION: R-R9K

<400> SEQUENCE: 9
gggcgggagt catacttgta tacggtggcg g                                    31

<210> SEQ ID NO 10
<211> LENGTH: 31
<212> TYPE: DNA
<213> ORGANISM: Artificial Sequence
<220> FEATURE:
<223> OTHER INFORMATION: F-R9K

<400> SEQUENCE: 10
ccgccaccgt atacaagtat gactcccgcc c                                    31

<210> SEQ ID NO 11
<211> LENGTH: 32
<212> TYPE: DNA
<213> ORGANISM: Artificial Sequence
<220> FEATURE:
<223> OTHER INFORMATION: F-E129G

<400> SEQUENCE: 11
ccacctacca gagcgggtat ctggcacacc gg                                   32

<210> SEQ ID NO 12
<211> LENGTH: 32
<212> TYPE: DNA
<213> ORGANISM: Artificial Sequence
<220> FEATURE:
<223> OTHER INFORMATION: R-E129G

<400> SEQUENCE: 12
ccggtgtgcc agatacccgc tctggtaggt gg                                   32

<210> SEQ ID NO 13
<211> LENGTH: 39
<212> TYPE: DNA
<213> ORGANISM: Artificial Sequence
<220> FEATURE:
<223> OTHER INFORMATION: 5'F-PD-ApaI

<400> SEQUENCE: 13
ggagggccca tgaaactcgt catcgccatc atcaagccc                            39

<210> SEQ ID NO 14
<211> LENGTH: 45
<212> TYPE: DNA
<213> ORGANISM: Artificial Sequence
<220> FEATURE:
<223> OTHER INFORMATION: 5'R-PD-MCS

<400> SEQUENCE: 14
```

```
tacggtaccg atcccgcat cgcaacaacg gggtcatcgc gaccc              45

<210> SEQ ID NO 15
<211> LENGTH: 45
<212> TYPE: DNA
<213> ORGANISM: Artificial Sequence
<220> FEATURE:
<223> OTHER INFORMATION: 3'F-PD-MCS

<400> SEQUENCE: 15
cgttctagaa ctagtccgct accaggtgta gcgatagccc aggtg             45

<210> SEQ ID NO 16
<211> LENGTH: 39
<212> TYPE: DNA
<213> ORGANISM: Artificial Sequence
<220> FEATURE:
<223> OTHER INFORMATION: 3'R-PD-BglII

<400> SEQUENCE: 16
tgtagatctc ggcgagatac ttgcgtttcg gcgttgtcg                    39

<210> SEQ ID NO 17
<211> LENGTH: 35
<212> TYPE: DNA
<213> ORGANISM: Artificial Sequence
<220> FEATURE:
<223> OTHER INFORMATION: PtxF-BamHI

<400> SEQUENCE: 17
ttgggatccc agcgcagccc tccaacgcgc catcc                        35

<210> SEQ ID NO 18
<211> LENGTH: 47
<212> TYPE: DNA
<213> ORGANISM: Artificial Sequence
<220> FEATURE:
<223> OTHER INFORMATION: PtxR-MCS

<400> SEQUENCE: 18
tctactagta agaattctcg cggtatccgt caaggaaaaa catggac           47

<210> SEQ ID NO 19
<211> LENGTH: 29
<212> TYPE: DNA
<213> ORGANISM: Artificial Sequence
<220> FEATURE:
<223> OTHER INFORMATION: TerF-EcoRI

<400> SEQUENCE: 19
gcggaattcc gcctgccgcc tgcacgcat                               29

<210> SEQ ID NO 20
<211> LENGTH: 29
<212> TYPE: DNA
<213> ORGANISM: Artificial Sequence
<220> FEATURE:
<223> OTHER INFORMATION: TerR-SpeI

<400> SEQUENCE: 20
tccactagtc aagggcatcg ggcgccggc                               29

<210> SEQ ID NO 21
<211> LENGTH: 35
<212> TYPE: DNA
<213> ORGANISM: Artificial Sequence
```

```
<220> FEATURE:
<223> OTHER INFORMATION: 5'F-PD2-SpeI

<400> SEQUENCE: 21
cgcactagtc tattccagcg gcgggtcgaa atggc                                    35

<210> SEQ ID NO 22
<211> LENGTH: 56
<212> TYPE: DNA
<213> ORGANISM: Artificial Sequence
<220> FEATURE:
<223> OTHER INFORMATION: 5'R-PD2-MCS

<400> SEQUENCE: 22
ccccaggcgg ccgctgtcta gagtggatcc caggccgatg cgtccgccgt gcaggc            56

<210> SEQ ID NO 23
<211> LENGTH: 36
<212> TYPE: DNA
<213> ORGANISM: Artificial Sequence
<220> FEATURE:
<223> OTHER INFORMATION: 3'F-PD2-XbaI

<400> SEQUENCE: 23
atctctagaa tgggcacctc ggccacgctg gcgctg                                  36

<210> SEQ ID NO 24
<211> LENGTH: 40
<212> TYPE: DNA
<213> ORGANISM: Artificial Sequence
<220> FEATURE:
<223> OTHER INFORMATION: 3'R-PD2-NotI

<400> SEQUENCE: 24
aagtatcgcg gccgatgagc gaaaccctgt tgaaagtatc                              40

<210> SEQ ID NO 25
<211> LENGTH: 30
<212> TYPE: DNA
<213> ORGANISM: Artificial Sequence
<220> FEATURE:
<223> OTHER INFORMATION: CmF-BamHI

<400> SEQUENCE: 25
cgcggatcct gatgtccggc ggtgcttttg                                         30

<210> SEQ ID NO 26
<211> LENGTH: 34
<212> TYPE: DNA
<213> ORGANISM: Artificial Sequence
<220> FEATURE:
<223> OTHER INFORMATION: FHAproF-BamHI

<400> SEQUENCE: 26
tctggatccc tgcgctggca cccgcggcgg gccg                                    34

<210> SEQ ID NO 27
<211> LENGTH: 42
<212> TYPE: DNA
<213> ORGANISM: Artificial Sequence
<220> FEATURE:
<223> OTHER INFORMATION: FHAR-MCS

<400> SEQUENCE: 27
gcctctagat tcatatgatt ccgaccagcg aagtgaagta at                           42
```

<210> SEQ ID NO 28
<211> LENGTH: 36
<212> TYPE: DNA
<213> ORGANISM: Artificial Sequence
<220> FEATURE:
<223> OTHER INFORMATION: PRNF-NdeI

<400> SEQUENCE: 28
ctggtcggca tatgaacatg tctctgtcac gcattg                                36

<210> SEQ ID NO 29
<211> LENGTH: 34
<212> TYPE: DNA
<213> ORGANISM: Artificial Sequence
<220> FEATURE:
<223> OTHER INFORMATION: PRNR-XbaI

<400> SEQUENCE: 29
gcctctagag cctggagact ggcaccggcc aagc                                  34

<210> SEQ ID NO 30
<211> LENGTH: 34
<212> TYPE: DNA
<213> ORGANISM: Artificial Sequence
<220> FEATURE:
<223> OTHER INFORMATION: PrnProF-BamHI

<400> SEQUENCE: 30
cggggatccg caccctggcc tgcggggcgg gacc                                  34

<210> SEQ ID NO 31
<211> LENGTH: 35
<212> TYPE: DNA
<213> ORGANISM: Artificial Sequence
<220> FEATURE:
<223> OTHER INFORMATION: PRNProR-NdeI

<400> SEQUENCE: 31
agacatgttc atatggatgc caggtggaga gcaga                                 35

<210> SEQ ID NO 32
<211> LENGTH: 26
<212> TYPE: DNA
<213> ORGANISM: Artificial Sequence
<220> FEATURE:
<223> OTHER INFORMATION: 5'F-int

<400> SEQUENCE: 32
ctagcgttcg cataccaaat ccttgc                                           26

<210> SEQ ID NO 33
<211> LENGTH: 26
<212> TYPE: DNA
<213> ORGANISM: Artificial Sequence
<220> FEATURE:
<223> OTHER INFORMATION: 5'RCM-int

<400> SEQUENCE: 33
ccgtaatatc cagctgaacg gtctgg                                           26

<210> SEQ ID NO 34
<211> LENGTH: 25
<212> TYPE: DNA
<213> ORGANISM: Artificial Sequence
<220> FEATURE:
<223> OTHER INFORMATION: 3'FCM-int

```
<400> SEQUENCE: 34
tctgtgatgg cttccatgtc ggcag                                              25

<210> SEQ ID NO 35
<211> LENGTH: 25
<212> TYPE: DNA
<213> ORGANISM: Artificial Sequence
<220> FEATURE:
<223> OTHER INFORMATION: 3'R-int

<400> SEQUENCE: 35
agcatgttgc ggtgttcccg gaatg                                              25

<210> SEQ ID NO 36
<211> LENGTH: 30
<212> TYPE: DNA
<213> ORGANISM: Artificial Sequence
<220> FEATURE:
<223> OTHER INFORMATION: 5'FPD-int

<400> SEQUENCE: 36
atgacggaaa gccgcatggg cattgggtcc                                         30

<210> SEQ ID NO 37
<211> LENGTH: 29
<212> TYPE: DNA
<213> ORGANISM: Artificial Sequence
<220> FEATURE:
<223> OTHER INFORMATION: 3'RPD-int

<400> SEQUENCE: 37
ttcgtacgtg ttcaggtgcc gattgccgg                                          29

<210> SEQ ID NO 38
<211> LENGTH: 26
<212> TYPE: DNA
<213> ORGANISM: Artificial Sequence
<220> FEATURE:
<223> OTHER INFORMATION: 5'FPD2-int

<400> SEQUENCE: 38
tgggctggct gttctggcac gaaacg                                             26

<210> SEQ ID NO 39
<211> LENGTH: 26
<212> TYPE: DNA
<213> ORGANISM: Artificial Sequence
<220> FEATURE:
<223> OTHER INFORMATION: 3'RPD2-int

<400> SEQUENCE: 39
ttcatcgaat cggcgctgat cctggc                                             26

<210> SEQ ID NO 40
<211> LENGTH: 26
<212> TYPE: DNA
<213> ORGANISM: Artificial Sequence
<220> FEATURE:
<223> OTHER INFORMATION: PRNF-int

<400> SEQUENCE: 40
aggtgcagcc atacatcaag gccagc                                             26

<210> SEQ ID NO 41
```

```
<211> LENGTH: 8
<212> TYPE: DNA
<213> ORGANISM: Artificial Sequence
<220> FEATURE:
<223> OTHER INFORMATION: R9K wild type

<400> SEQUENCE: 41 tacaagta                                                                    8

<210> SEQ ID NO 42
<211> LENGTH: 9
<212> TYPE: DNA
<213> ORGANISM: Artificial Sequence
<220> FEATURE:
<223> OTHER INFORMATION: E129G wild type

<400> SEQUENCE: 42 agcgggtat                                                                   9

<210> SEQ ID NO 43
<211> LENGTH: 54
<212> TYPE: DNA
<213> ORGANISM: Artificial Sequence
<220> FEATURE:
<223> OTHER INFORMATION: WWD (316)

<400> SEQUENCE: 43
acgatcctcc cgccaccgta tacaagtatg actcccgccc gccggaggac gttt              54

<210> SEQ ID NO 44
<211> LENGTH: 54
<212> TYPE: DNA
<213> ORGANISM: Artificial Sequence
<220> FEATURE:
<223> OTHER INFORMATION: Wild type (159)

<400> SEQUENCE: 44
acgatcctcc cgccaccgta taccgctatg actcccgccc gccggaggac gttt              54

<210> SEQ ID NO 45
<211> LENGTH: 51
<212> TYPE: DNA
<213> ORGANISM: Artificial Sequence
<220> FEATURE:
<223> OTHER INFORMATION: Consensus (316)

<400> SEQUENCE: 45
acgatcctcc cgccaccgta tactatgact cccgcccgcc ggaggacgtt t                 51

<210> SEQ ID NO 46
<211> LENGTH: 54
<212> TYPE: DNA
<213> ORGANISM: Artificial Sequence
<220> FEATURE:
<223> OTHER INFORMATION: WWD (334)

<400> SEQUENCE: 46
ggcgcgctgg ccacctacca gagcgggtat ctggcacacc ggcgcattcc gccc              54

<210> SEQ ID NO 47
<211> LENGTH: 54
<212> TYPE: DNA
<213> ORGANISM: Artificial Sequence
<220> FEATURE:
<223> OTHER INFORMATION: Wild type (415)

<400> SEQUENCE: 47
```

-continued

```
ggcgcgctgg ccacctacca gagcgaatat ctggcacacc ggcgcattcc gccc    54
```

<210> SEQ ID NO 48
<211> LENGTH: 52
<212> TYPE: DNA
<213> ORGANISM: Artificial Sequence
<220> FEATURE:
<223> OTHER INFORMATION: Consensus (415)

<400> SEQUENCE: 48

```
ggcgcgctgg ccacctacca gagcgtatct ggcacaccgg cgcattccgc cc    52
```

MODIFIED *BORDETELLA PERTUSSIS* STRAINS

CROSS-REFERENCE TO RELATED APPLICATIONS

This application is a Continuation Application of International Application No. PCT/TH2012/000052, which has an International Filing Date of Dec. 20, 2012 and designates the United States of America, and which claims priority to South Africa Application No. 2011/09417 filed Dec. 21, 2011 the disclosures of which are hereby expressly incorporated by reference in their entirety and are hereby expressly made a portion of this application.

REFERENCE TO SEQUENCE LISTING

The present application incorporates by reference the sequence listing submitted as an ASCII text filed via EFS-Web on Jun. 5, 2014. The Sequence Listing is provided as a file entitled Seq_List.txt, created on Jun. 5, 2014, which is approximately 13 Kb in size.

BACKGROUND

1. Field of the Invention

The present invention describes the construction of recombinant *Bordetella pertussis* strains derived from a parent strain designated Tohama and using vector pSS4245 for integration of mutations and additional copies of genes.

2. Description of Related Art

Pertussis or whooping cough is a severe infant disease caused by *Bordetella pertussis* infection of the upper respiratory tract [1]. Vaccines have been available for decades, which consist of killed whole cells of *B. pertussis*. They are administered as trivalent Diphtheria-Tetanus-Pertussis combination or newer combinations providing also immunity against Hepatitis B and *Haemophilus influenzae* type b invasive disease [2]. The use of whole-cell vaccines has been reduced, discouraged or even banned in a few countries due to their questionable safety profile, which is due to high levels of endotoxin and other bacterial toxins associated with the killed whole cells [3, 4].

Acellular vaccines, named after the fact that they do not contain whole cells but only partially or extensively purified bacterial antigens, were introduced in Japan in 1981 [5]. The higher purity of the component antigens in acellular vaccines translated to an improved clinical safety profile. These vaccines were introduced in the mid-90s in industrialized countries after extensive field trials which demonstrated their safety and efficacy [6]. A broader introduction by WHO into the Expanded Program of Immunization was, however, hampered by the significantly higher cost of acellular vaccines.

A major virulence factor of *B. pertussis* is Pertussis Toxin (PT) [7, 8] and pertussis toxoid (PTd) is the principal antigen in acellular vaccines [8]. Unlike Diphtheria and Tetanus toxins, which can be inactivated by simple treatment with formaldehyde, PT proved more difficult to inactivate by chemical means [9]. Currently different inactivation processes are in use for commercial production. All have in common extensive denaturation of PT caused by the chemical treatment. Two candidate vaccines were explored using a genetically inactivated toxin (rPT) [10-12] and one of these candidates was included in a field efficacy trial [11-12].

Vaccines containing rPT are, however, not yet available.

SUMMARY

According to a first embodiment of the invention, there is provided a genetically modified *Bordetella pertussis* Tohama strain, wherein the Pertussis Toxin S1 gene of the Tohama strain having ATCC accession number BAA-589 has Arg9→Lys9 and Glu129→Gly129 mutations and does not include an integrated antibiotic resistance gene as a result of the mutations, wherein the modified strain is capable of expressing detoxified Pertussis Toxin (rPT).

Vector pSS4245 may be used to introduce the S1 mutations without integration of an antibiotic resistance gene.

The strain may have been further modified by integration of a copy of the ptx operon into a non-functional region of the chromosome of the modified Tohama strain using vector pSS4245, wherein the integrated ptx operon comprises a set of S2-S5 genes and a S1 gene which has been modified to includes the mutations Arg9→Lys9 and Glu129→Gly129, the modified strain thereby having two ptx operons which are positioned apart in the Tohama chromosome without an integrated antibiotic resistance gene, and being capable of expressing enhanced levels of detoxified Pertussis Toxin relative to a strain with only one ptx operon.

The copy of the ptx operon may be integrated within or between non functional pseudogenes.

The copy of the ptx operon may be integrated between a putative ammonium transporter pseudogene amtB and a putative autotransporter pseudogene.

The integrated copy of the ptx operon may be under the control of a ptx-ptl operon promoter.

An additional copy of the ptl operon may not be incorporated into the strain.

The strain may include more than one inserted copy of the modified ptx operon.

The strain may be further modified by integration of a copy of a prn gene encoding Pertactin into a non-functional region of the chromosome of the modified Tohama strain using vector pSS4245, the modified Tohama strain thereby having two prn genes which are positioned apart in the Tohama chromosome without integration of an antibiotic resistance gene, and the modified Tohama strain being capable of expressing enhanced levels of Pertactin relative to a strain with only one prn gene.

The inserted prn gene may be located within or between non functional pseudogenes.

The copy of the prn gene may be integrated between a pseudo-putative glutathione S-transferase gene and a pseudo putative aspartate racemase gene.

The copy of the prn gene may be under the control of a prn promoter.

The strain may comprise more than one inserted copy of the prn gene, and may comprise at least two modified ptx operons and at least two prn genes.

Preferably, functional genes of the wild-type Tohama strain have not been removed, replaced or inactivated.

According to a second embodiment of the invention, there is provided a method of producing a modified *B. pertussis* strain, the method comprising the step of replacing the catalytic subunit S1 gene in a *B. pertussis* strain designated Tohama and having ATCC accession number BAA-589 with a S1 gene which includes the mutations Arg9→Lys9 and Glu129→Gly129 wherein vector pSS4245 is used to replace the unmodified S1 gene with the modified S1 gene, thereby resulting in integration of the modified gene without integration of an antibiotic resistance gene and a strain being produced which is capable of expressing detoxified Pertussis Toxin (rPT).

The method may further include the step of integrating a copy of the ptx operon into a non-functional region of the chromosome of the modified Tohama strain using vector pSS4245, wherein the integrated ptx operon comprises a set of S2-S5 genes and a S1 gene which has been modified to includes the mutations Arg9→Lys9 and Glu129→Gly129 thereby producing a modified Tohama strain which has two ptx operons which are positioned apart in the Tohama chromosome without integration of an antibiotic resistance gene, the modified Tohama strain being capable of expressing enhanced levels of detoxified Pertussis Toxin relative to a strain with only one ptx operon.

The method may further include the step of integrating a copy of a prn gene encoding Pertactin into a non-functional region of the chromosome of the modified Tohama strain using vector pSS4245, thereby producing a modified Tohama strain which has two prn genes which are positioned apart in the Tohama chromosome without integration of an antibiotic resistance gene, the modified Tohama strain being capable of expressing enhanced levels of Pertactin relative to a strain with only one prn gene.

More than one copy of the modified ptx operon and/or the prn gene may be inserted into the chromosome of the Tohama strain.

According to a third embodiment of the invention, there is provided a method of producing Bordetella pertussis antigens which comprises the steps of:
 culturing a genetically modified B. pertussis Tohama strain described above in a culture medium to effect expression of the antigens, wherein the antigens include detoxified Pertussis Toxin (rPT), Pertactin and Filamentous Hemagglutinin (FHA) encoded by genes present in the strain; and recovering the antigens.

The PT and FHA antigens may be recovered from the culture medium, while the PRN antigen may be recovered in part from the culture medium and in part from cells by extraction procedures such as high temperature treatment.

Agglutinogens 2 and/or 3 may also be expressed and recovered.

According to a fourth embodiment of the invention, there is provided an antigen produced by the method described above.

The antigen may be used in preventing Pertussis infection in a subject, and in particular, in manufacturing an acellular vaccine for preventing Pertussis infection.

According to a fourth embodiment of the invention, there is provided an acellular vaccine comprising an antigen produced as described above. The antigen may be detoxified Pertussis Toxin and/or Pertactin. The vaccine may further include FHA, Agglutinogen 2 and/or Agglutinogen 3 and/or antigens for preventing or treating other diseases, including one or more of Diphtheria, Tetanus, Hepatitis B, Poliomyelitis and Hemophilus influenzae type b.

BRIEF DESCRIPTION OF THE FIGURES

FIG. 3: Allelic exchange procedure. A: Double recombination events leading to the replacement of the S1 gene by a chloramphenicol resistance marker. B: Double recombination events leading to the re-insertion of the modified S1 gene in its original location.

DETAILED DESCRIPTION OF CERTAIN EMBODIMENTS OF THE INVENTION

Figure 1:
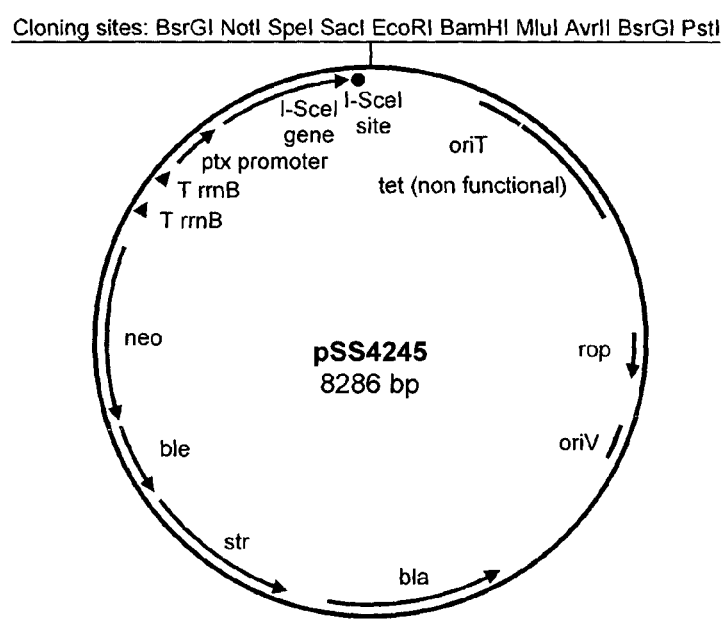
FIG. 1: Schematic structure of the allelic exchange vector pSS4245

Recombinant Bordetella pertussis strains derived from a parent strain designated Tohama are described herein. The new strains are obtained by homologous recombination using an allelic exchange vector pSS4245 [41]. This vector allows the replacement of sections of the bacterial chromosome without leaving any accessory mutations.

The genes for PT, FHA and pertactin (PRN) have been cloned and sequenced [35-39]. Pertussis toxin is a complex protein composed of six polypeptide subunits, encoded by five different structural genes expressed from a single promoter. Its enzymatic and most of its toxic activities are mediated by its subunit S1, while its cell-binding and mitogenic properties are due to the other subunits, which form the B-subunit.

In a first embodiment, the segment encoding PT subunit S1 was replaced to introduce two mutations causing the inactivation of the toxic activity. In a second embodiment, a second copy of the ptx cluster of the five PT structural genes of the ptx-ptl operon with their promoter and the ptl terminator and containing the above mutations was inserted elsewhere on the chromosome. The organization of ptl auxiliary genes present in the ptx-ptl operon was not modified. This strain produced increased amounts of rPT. In a third embodiment, a second copy of the prn gene was inserted on the chromosome. In both cases, abandoned gene loci were selected as insertion site to avoid the introduction of unwanted genetic alterations and the antigen expression was driven by the autologous promoters, thus subject to the same regulation as in the parent Tohama strain.

PT and even more so PRN are the limiting antigens in high-density cultures, while FHA is naturally overproduced by B. pertussis under these conditions. PRN however could be obtained in high yield from recombinant E. coli or Pichia pastoris [14, 15] whereas only PT subunits could be expressed in E. coli but failed to assemble to the mature toxin and were insufficiently immunogenic to be considered as potential vaccine candidates [16]. It is now understood that assembly and secretion of the mature toxin requires several auxiliary genes discovered at a later stage, which are part of the ptl section of the ptx-ptl operon [17].

Although enhanced production by manipulation of gene copy number has been reported to enhance the production of bacterial toxins [18, 19], in particular PT [20], this has been largely used with multi-copy plasmid vectors or genes were tandemly repeated. This may have consequences on strain genetic stability, in particular in a production setting. For example, the B. pertussis strains generated by Lee et al. [40] using multi-copy plasmid vectors did not show any increase in PT production, and the plasmid was rearranged, the PT operon deleted or the transconjugants underwent conversion to an avirulent phase.

Contrary to the allelic exchange vectors used earlier in B. pertussis, pSS4245 does not require or leave auxiliary mutations on the chromosome, in particular the mutation affecting rpsL which results from the selection of spontaneous streptomycin resistant mutants as required in earlier allelic exchange procedures [22]. Such mutations affecting housekeeping genes may impair virulence and hence the expression of virulence factors including PT, FHA and PRN. The strains of the present invention produce unaltered levels of the other antigens, in particular FHA, and can be used for the production of affordable acellular Pertussis vaccines.

Results
Mutation of S1 Gene in B. pertussis Chromosome

To introduce the two mutations R9K and E129G into subunit S1, a two stage approach was used, to avoid the possibility of recombination in the region between the two mutations, which would cause the loss of one of the mutations. This approach also allows for the selection of the desired colonies by simple replica plating on selective media. First two E. coli vectors were constructed in pBluescript II SK+ where the wild type S1 gene was replaced by a chloramphenicol resistance gene ($Cm^R$) (FIG. 2A) or by a modified S1 gene including the desired mutations (FIG. 2B), both flanked by 1.2-1.5 kB of the S1 upstream and downstream regions. These vectors were then processed and their inserts introduced into pSS4245. These derivatives were transferred into E. coli SM10 for conjugative transfer and allelic exchange into B. pertussis strain Tohama. The plasmid pSS5Cm3 generated a replacement of the S1 gene by the $Cm^R$ marker (FIG. 3A). The plasmid pSS5S13-9K-129G restored the S1 gene into its original location, now with the two desired mutations (FIG. 3B). After selection of isolates on selective media, the integration of the $Cm^R$ and modified S1 genes at the expected position was confirmed by PCR amplification (data not shown). The integration of the mutated S1 gene at the expected location was evident as confirmed by PCR with specific primers which could bind the upstream 5' and 3' downstream flanking regions and internally in the S1 gene (data not shown). The mutations in the S1 gene of the clone selected for further elaboration was confirmed by DNA sequencing. The new strain was designated Bp-WWC.

Insertion of a Second Integration Site for a Second Set of PT Structural Genes

Figure 4:
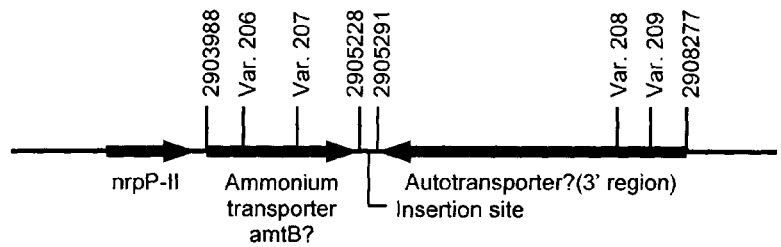
FIG. 4: Vectors for the insertion of second copy of the ptx operon into the B. pertussis chromosome. A: The insertion site for a second copy of the ptx operon was selected between two abandoned genes carrying each two frameshift mutations. B: Allelic exchange elements used to insert a chloramphenicol marker into the selected site. C: Schematic structure of the ptx operon with its original promoter. The ptx-ptl terminator was cloned and inserted past the S3 gene. This cluster was finally integrated into the SS4245 derivative to replace the chloramphenicol marker and generate the second allelic exchange event to insert the second copy of the PT structural genes.
Figure 4:
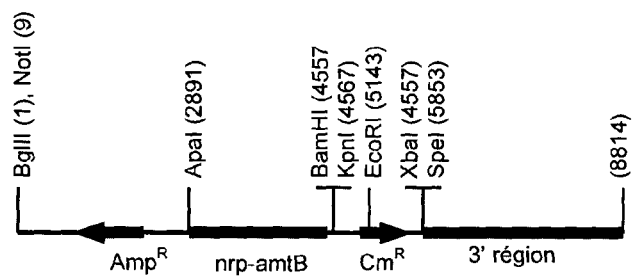
Figure 4:
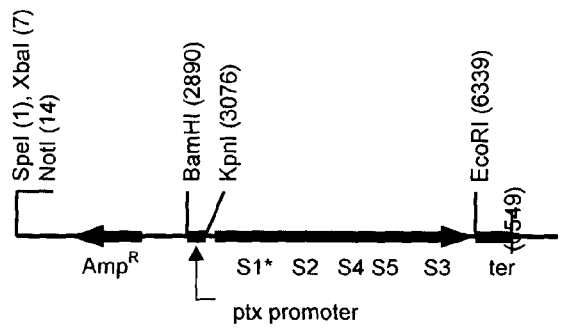

Initial attempts to increase PT expression by inserting the whole ptx-ptl operon on a multicopy plasmid compatible with B. pertussis failed to deliver useful strains, suggesting that the overexpression of PT is potentially toxic and must remain within certain limits to obtain viable strains. In order to increase the PT toxin yield, a second set of PT structural gene was introduced into the Bp-WWC chromosome. To identify an insertion target site, the sequence of the B. pertussis Tohama genome was scanned and many pseudo-genes were identified. The DNA sequence between a putative ammonium transporter gene and a putative auto-transporter gene was selected for insertion (posn. 2,903,988-2,905,228 and 2,905,291-2,908,277). These genes carry each frameshift mutations which ruin their functionality (FIG. 4A). The general strategy outlined in the preceding section was followed. First the E. coli vector pSKPD5Cm3 was constructed by inserting the $Cm^R$ gene within the regions flanking the selected integration site (FIG. 4B). After insertion of the sequences of interest into pSS4245, allelic exchange was selected by the $Cm^R$ marker. Integration of the $Cm^R$ gene at designed position was confirmed by PCR (data not shown). In the second vector the 5 PT structural genes S1 ... S3 were inserted with the ptx promoter and the ptl terminator following the S3 gene within the same flanking regions to generate the vector pSKptxter including the two mutations in S1 (FIG. 4C). Allelic exchange into the target integration site inserted a second copy of the functional cluster of the PT structural genes into Bp-WWC strain. The new strain was designated Bp-WWD. The result of integration was verified by amplification using primers binding to the upstream or downstream regions and inside the ptx operon, which showed the expected integration without disruption of the regions where recombination had occurred.

Sequencing of the S1 Gene and Identification of the R9K and E129G Mutations

Figure 5:
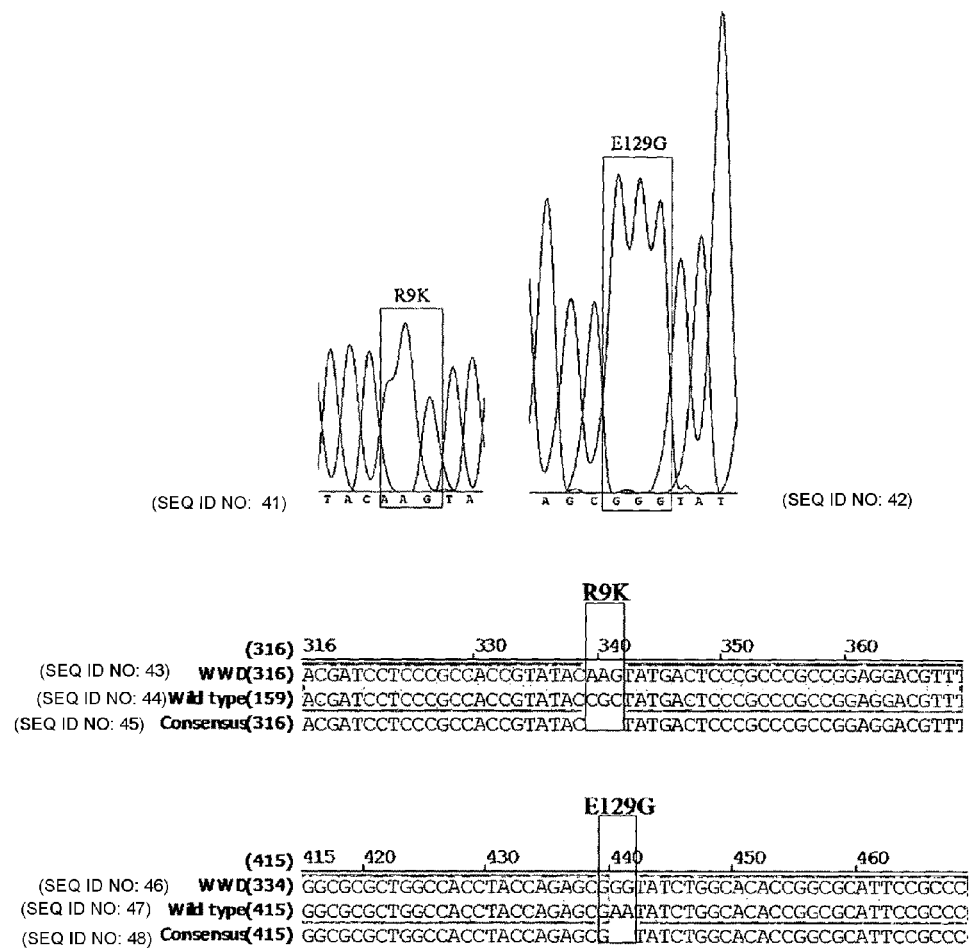
FIG. 5: Identification of the R9K and E129G mutations in Bp-WWC and Bp-WWD. Raw sequence data around the mutations are shown for strain Bp-WWD, which has two copies of the PT structural cluster. The corresponding sequence alignments are shown for B. pertussis Tohama (consensus sequence) and derivatives Bp-WWC and Bp-WWD.

Automated sequencing was applied to confirm the presence of the desired mutations. In the case of strain Bp-WWD which has two integrated copies of the S1 gene, PCR amplification yields in principle a mix of the copies of the two genes. An unexpected point mutation in one of the inserts would appear as a double nucleotide assignment at the corresponding position. The single peak of fluorescence signal at the R9K and E129G positions indicated the correct sequence on Bp-WWC and that the two copies of S1 in Bp-WWD had identical mutations. The sequence around the two desired mutations is reported in FIG. 5, which shows the sequencing records for strain Bp-WWD and the sequence alignments for wt Tohama, Bp-WWC and Bp-WWD.

Insertion of a Second Copy of the PRN Genes into Bp-WWD Strain

Figure 6:
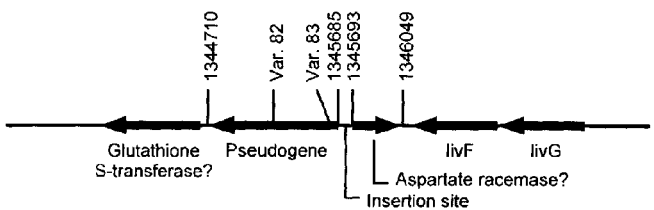
FIG. 6: Vectors for the insertion of second copy of the prn gene into the B. pertussis chromosome A: The insertion site for a second copy of the prn gene was selected between two abandoned genes carrying frameshift mutations and a deletion. B: Schematic structure of the prn gene under control of fha promoter and flanking with target integration site. C: Schematic structure of the prn gene under control of its own promoter and flanking with target integration site.
Figure 6:
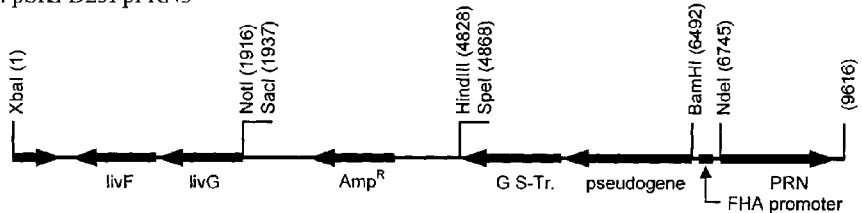
Figure 6:
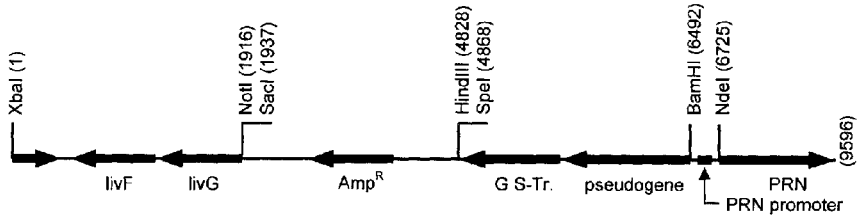

Due to the limitation of PRN production, a second copy of prn structural gene under control of the fha promoter and its own terminator was introduced into Bp-WWD chromosome between the two pseudogenes of putative glutathione S-transferase pseudogene and a putative aspartate racemase (FIG. 6A). The pSKPD2Cm3 E. coli vector was constructed where the $Cm^R$ gene was inserted between the upstream and downstream regions flanking the selected insertion site. Another vector was constructed using the same flanking regions and the prn gene under the control of the FHA promoter (FIG. 6B). After insertion of the $Cm^R$ marker in the desired location, the $Cm^R$ gene was replaced by the prn functional block using the usual allelic exchange selection and screening procedures.

The B. pertussis strains isolated from this construction did not express PRN and the level of the other antigens was eventually not detectable. It was tentatively concluded that the PRN product is toxic if overproduced under the control of the stronger FHA promoter and only escape mutants having lost the capacity to produce PRN or all virulence factors were viable. It was therefore decided to introduce the natural prn promoter in place of the fha promoter. pSKPD25FpPRN3 was used to replace the FHA promoter by the original PRN promoter to generate a functional block with its own natural promoter and terminator (FIG. 6C). This functional block was inserted at the selected site by the usual allelic exchange procedure to obtain a strain with a second non-tandemly repeated copy of the prn gene under control of its own promoter. The expected insertion was confirmed by PCR amplification with primers binding to the flanking regions and internally in the prn gene. This strain was normally viable and was designated Bp-WWE.

Genetic Stability of PT and PRN Constructs

The strain Bp-WWE was cultured and serially subcultured in MSS medium to reach approximately a total of 50 generations. The last culture was diluted and plated on MSS-agar. Thirty isolated colonies were randomly picked. Thirty colonies were analyzed for their S1 and prn genes by PCR (data not shown). The result showed that all colonies contained two copies of S1 and prn genes at the expected positions.

Expression of PT and FHA in Shake Flask

The production of PT and FHA in shake flask cultures was analyzed by ELISA. Shake flasks cultures were all in Modified Stainer-Scholte medium (MSS) containing heptakis(2,6-O-dimethyl)-β-cyclodextrin [23, 24]. Results of strains Bp-WWC and Bp-WWD are shown in Tables 1 and 2. The production of PT was about doubled in strain Bp-WWD as compared to Bp-WWC and wt. Tohama showing the expected correlation of the level of expression and the number of copies of the structural gene cluster.

TABLE 1

PT production by strains Tohama, Bp-WWC and Bp-WWD. Cells were grown in shake flasks for 48 hrs (expt. #1) or 20-24 hrs (expt. #2) in MSS medium. The results of two independent flasks are shown for expt. #2. After harvesting by centrifugation, the supernatants were assayed by a direct ELISA with rabbit a polyclonal antibodiy (expt. #1) or by a sandwich ELISA using a rabbit polyclonal antibody as capture reagent and an S2-specific monoclonal (Abcam) for detection.

| | | PT, µg/mL | |
| --- | --- | --- | --- |
| Strain | Medium | Expt. #1 | Expt. #2 |
| Tohama wt | MSS | 2.24 | nd |
| Bp-WWC | MSS | 2.64 | 2.1-2.6 |
| Bp-WWD | MSS | 5.25 | 4.5-5.3 |

TABLE 2

PT and FHA production by strains Bp-WWC and Bp-WWD abd Bp-WWE. Cells were grown in shake flasks for 24 or 36 hrs in MSS medium. After harvesting by centrifugation, the supernatants were assayed for PT and FHA by a sandwich ELISA using a rabbit polyclonal antibody as capture reagent and an S2-specific monoclonal (Abcam) or an FHA monoclonal regent (NIBSC) for detection.

| | | PT, µg/mL | | FHA, µg/mL | |
| --- | --- | --- | --- | --- | --- |
| Strain | Medium | 24 hrs | 36 hrs | 24 hrs | 36 hrs |
| Bp-WWC | MSS | 3.16 | 2.96 | 10.9 | 20.5 |
| Bp-WWD | MSS | 4.21 | 4.03 | 5.7 | 12.8 |
| Bp-WWE | MSS | 4.63 | 4.97 | 11.4 | 18.9 |

Expression of PRN in Shake Flask

The production of PRN in shake flask cultures of Bp-WWC, Bp-WWD and Bp-WWE grown in MSS medium. As PRN release from its membrane-bound precursor is the result of an imprecise cleavage by unidentified proteases [25], PRN expression was determined by western blot densitometric analysis to evaluate also the integrity of the antigen. It was also found that in high-density fermentor cultures, a significant fraction of PRN is spontaneously released into the culture supernatant from the membrane-bound precursor (unpublished observations). Whether this property was modified by the genetic modifications introduced was therefore investigated. PRN was assayed on the clarified culture supernatants and on the 60° C. extract of the separated cells. The results are shown in Table 3. The amount of PRN toxin in Bp-WWC and Bp-WWD was similar. A two-fold increase was found in Bp-WWE showing again a good correlation of the level of expression and the gene copy number. With Bp-WWE however, the fraction of PRN found in the culture supernatant was increased although in these flask cultures, the supernatant fraction remained small or negligible.

TABLE 3

PRN production by strains Bp-WWC, Bp-WWD and Bp-WWE. Cells were grown in shake flasks for 48 hrs. The supernatant and cells were separated by centrifugation. The cells were suspended into the original culture volume of extraction buffer and heated to 60° C. for 30 min, then centrifuged again to collect the extract. PRN was assayed in both fractions by Western blot.

| | PRN (µg/mL) | | |
| --- | --- | --- | --- |
| Strain | Extract, µg/mL | Supernatant, µg/mL (%) | Total, µg/mL |
| Bp-WWC | 3.34 | 0.08 (2.3%) | 3.42 |
| Bp-WWD | 3.04 | 0.04 (1.3%) | 3.08 |
| Bp-WWE | 6.77 | 0.60 (8.2%) | 7.37 |

The level of PRN in all these flask cultures was well below the concentration of PT and FHA in similar conditions. Although PRN is produced less efficiently than PT, this result does not reflect the findings generally made in high density fermentor cultures. This discrepancy is explained by the fact that PRN is a cell surface protein whereas PT and FHA are secreted and by necessity in shake flasks, the growth time is limited to avoid cell lysis and antigen degradation, hence the biomass growth time is limited 24-36 hrs and cultures can reach a maximum $OD_{650}$ of 1-1.5, which correspondingly limits the primary source of PRN.

Assessment of PT Inactivation

Figure 7:
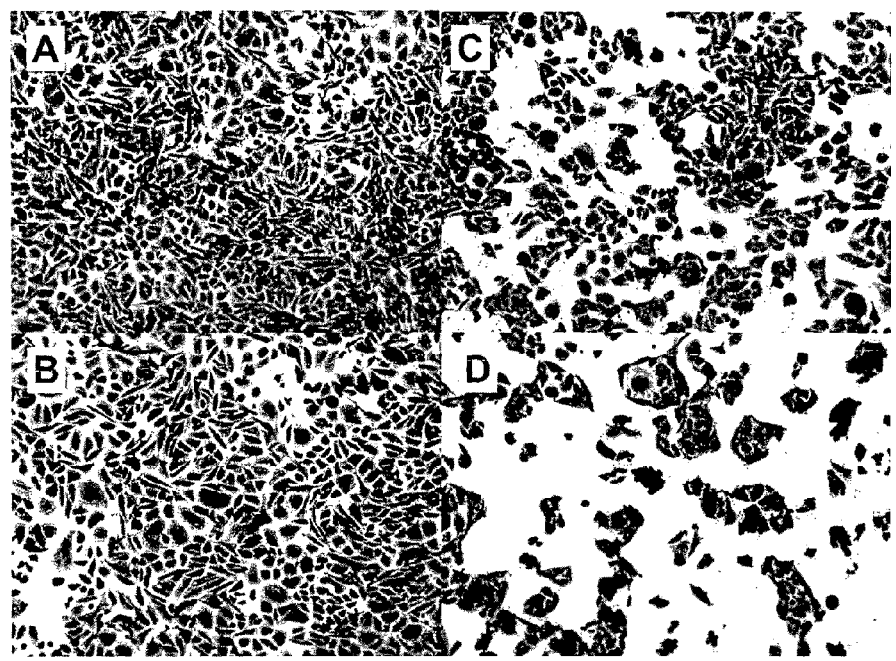
FIG. 7: CHO cell clustering test. The cells were grown to near confluence then dilutions of PT were added and the clustering was scored after 2 days. A: 800 ng PT (strain Bp-WWC). B: Control, no PT added. C: 2.6 pg wt PT (strain Tohama) corresponding to the threshold of detection. D. 43 pg wt PT (strain Tohama).

PT was purified from culture supernatants by a modification of the process of Ozcengiz [26] where the initial ammonium sulphate precipitation was replaced by ligand exchange chromatography [27, 28]. The toxicity of the PT toxin from wild type *B. pertussis* and Bp-WWC (genetically inactivated PT) was analysed and compared by CHO cell clustering testing [29]. This test has a much higher sensitivity than other functional assays reported for PT. The native toxin, purified from strain *B. pertussis* Tohama demonstrated a clustering endpoint at 2.6 pg per well. The genetically inactivated PT did not promote clustering at the highest concentrations obtained in this test, namely 0.8-1.6 µg per sample (FIG. 7). This test can therefore demonstrate a reduction of toxicity by a factor of $5 \times 10^5$ to $10^6$, considering the limitations imposed by the low solubility of PT. The result show that PT toxin from Bp-WWC was successfully inactivated by five nucleotide replacements resulting in two amino acid substitutions in PT subunit S1.

Discussion

Unmarked gene insertion and replacement in these experiments were successful by using pSS4245 as the vector in *B. pertussis*. After a second homologous recombination causing the excision of the plasmid, no antibiotic gene marker or any scar was left in the chromosome when compared with the cre-lox system [30] or earlier allelic exchange procedures used in *Bordetella* [22]. Overproduction of genetically deactivated PT toxin was reported in 1992 [20] by using tandem repeats of ptx genes or another copy inserted into the fha gene. The resulting strain overproduced PT up to 80 mg/L. Tandemly repeated genes are a known potential cause of genetic instability. For this reason, the genome sequence of *B. pertussis* was scanned to find out suitable integration sites. The DNA position between two terminators of pseudo-genes was selected as integration sites for the ptx cluster. The copy number for the PT structural cluster was limited to two, as overproduction of these virulence factors places a burden on the cell metabolism, which can result in slower growth rate and eventually genetic instability, as the preliminary attempts had suggested.

The inventors reported that over-expression of prn gene by the fha promoter to drive higher expression was apparently toxic to the *B. pertussis* cell, possibly in association with higher PT expression. Their findings did not confirm the increased PRN expression by replacement of the PRN promoter by a stronger promoter [21]. Therefore increasing the gene copy number under the control of the native PRN promoter was the approach selected. The fha promoter of the second gene copy was replaced by the native prn promoter to generate a strain with a second copy of the PRN gene and its native promoter inserted into another location on the chromosome. The toxicity of PRN to the host cell was also reported in *E. coli* [31]. The fha promoter was then replaced by the native prn promoter, the resulting strain exhibited normal growth in shaker flasks and produced correspondingly double quantities of PRN. The distribution of PRN between culture supernatant and cell extract was somewhat modified with a larger fraction of the total PRN in the supernatant although in shake flasks the quantities spontaneously released into the supernatant are minimal.

Although the growth in shake flask is limited due to the rapid pH rise and intoxication resulting from the release of ammonia by the metabolism of the glutamate carbon source [32], it provides a useful indication of the strain potential under optimized fermentor conditions. The construction of stable strains with enhanced expression of PT (Bp-WWD) or of the two limiting antigens PT and PRN (Bp-WWE) was demonstrated. With enhanced production of PT alone, Bp-WWD can only generate insufficient quantities of PRN and in this case, the use of an independent supply of PRN in recombinant *E. coli* or *P. pastoris* would be indicated. As the level of the two antigens PT and PRN has been equally increased with Bp-WWE, matching quantities of the two antigens are expected to be obtained also in high density cultures, thereby simplifying production operations.

Conclusions

*B. pertussis* strains which contain a genetically inactivated S1::R9K-E129G subunit of PT were constructed without any marker or scar left in their chromosome. A two fold increase of PT toxin was found in shake flasks by integration of 5 structural genes (ptx with S1 mutated) under the control of the ptx-ptl operon promoter and ptl terminator between two pseudo-genes on the chromosome. Inactivation of PT was confirmed by CHO cell clustering assay. Moreover PRN production was increased by integration of a second copy of the prn gene between other pseudo-genes elsewhere on the chromosome. The strains were found genetically stable in shake flask subcultures reproducing a higher number of generations than would be necessary in a large scale (>1000 L) fermentation. These strains, in particular Bp-WWE where the relative quantities of the PT and PRN antigens match the composition of vaccines, should prove useful to enable the production of affordable acellular Pertussis vaccines, contributing to the cost reduction by the lower dosage required by native antigens for adequate immunogenicity and the higher productivity of the strain for the two limiting antigens PT and PRN.

Methods

Bacterial Strains, Plasmids and Culture Conditions

All chemicals and reagents used in this study were either molecular biology or analytical grade. Chemicals were purchased from Merck and Sigma. Bacterial culture media were obtained from Difco (USA) and Merck (Germany). Restriction and modifying enzymes were purchased from New England Biolabs (USA).

*E. coli* DH5α (Invitrogen, USA) was used as a cloning host. This strain was grown at 37° C. in Luria Bertani medium (LB). The *E. coli* DH5α transformants were grown in LB supplemented with appropriate antibiotics: amplicillin (50 µg/ml) or chloramphenicol (15 µg/ml). *E. coli* SM10 was obtained from Dr. Earle S. Stibitz (Division of Bacterial, Parasitic, and Allergenic Products, Center for Biologics Evaluation and Research, Food and Drug Administration, USA) and used as a conjugation donor strain. This strain was grown at 37° C. in LB supplemented with kanamycin (50 µg/ml). The *E. coli* SM10 transformants were grown in LB supplemented with kanamycin (50 µg/ml), amplicillin (50 µg/ml) and neomycin (10 µg/ml). *B. pertussis* Tohama was obtained from ATCC and has ATCC accession number BAA-589 (*Bordetella pertussis* Tohama Ph. I chromosome Accession No. NC_002929, EMBL/GenBank Accession No. BX470248, sequence available from the Wellcome Trust Sanger Institute [42]).

*B. pertussis* strains were grown at 35° C. on Bordet-Gengou (BG) agar or modified Stainer-Scholte medium (MSS). Plasmid pBluescript II SK+ was obtained from Stratagene, USA, pSS4245 was obtained from Dr. Earle S. Stibitz and pACYC184 was obtained from New England Biolabs (USA).

TABLE 4

Primers

| Name | Sequence | |
|---|---|---|
| 5'F-PT-SalI | GCGGTCGACGGCGCGCAATGCGGCGCGGAC | Seq ID No: 1 |
| 5'R-PT-MCS | GGGGGCGGCCGCGAGATCTCTCTAGACGGTA CCATCGCGCGACTTTGCGCCGAAGGA | Seq ID No: 2 |
| 3'F-PT-XbaI | CGTTCTAGACCTGGCCCAGCCCCGCCCAAC | Seq ID No: 3 |
| 3'R-PT-BglII | GGCAGATCTGCAGTTCGAGCAGATCGCCGG | Seq ID No: 4 |
| CmF-KpnI | CGCGGTACCTGATGTCCGGCGGTGCTTTTG | Seq ID No: 5 |
| CmR-XbaI | AATCTAGATATCGTCAATTATTACCTCCAC | Seq ID No: 6 |

TABLE 4-continued

| Primers | | |
|---|---|---|
| Name | Sequence | |
| S1F-PT-KpnI | GATGGTACCGGTCACCGTCCGGACCGTGCT | Seq ID No: 7 |
| S1R-PT-XbaI | CAGGTCTAGAACGAATACGCGATGCTTTCG | Seq ID No: 8 |
| R-R9K | GGGCGGGAGTCATACTTGTATACGGTGGCGG | Seq ID No: 9 |
| F-R9K | CCGCCACCGTATACAAGTATGACTCCCGCCC | Seq ID No: 10 |
| F-E129G | CCACCTACCAGAGCGGGTATCTGGCACACCGG | Seq ID No: 11 |
| R-E129G | CCGGTGTGCCAGATACCCGCTCTGGTAGGTGG | Seq ID No: 12 |
| 5'F-PD-ApaI | GGAGGGCCCATGAAACTCGTCATCGCCATCATCAAGCCC | Seq ID No: 13 |
| 5'R-PD-MCS | TACGGTACCGGATCCCGCATCGCAACAACGGGGTCATCGCGACCC | Seq ID No: 14 |
| 3'F-PD-MCS | CGTTCTAGAACTAGTCCGCTACCAGGTGTAGCGATAGCCCAGGTG | Seq ID No: 15 |
| 3'R-PD-BglII | TGTAGATCTCGGCGAGATACTTGCGTTTCGGCGTTGTCG | Seq ID No: 16 |
| PtxF-BamHI | TTGGGATCCCAGCGCAGCCCTCCAACGCGCCATCC | Seq ID No: 17 |
| PtxR-MCS | TCTACTAGTAAGAATTCTCGCGGTATCCGTCAAGGAAAAACATGGAC | Seq ID No: 18 |
| TerF-EcoRI | GCGGAATTCCGCCTGCCGCCTGCACGCAT | Seq ID No: 19 |
| TerR-SpeI | TCCACTAGTCAAGGGCATCGGGCGCCGGC | Seq ID No: 20 |
| 5'F-PD2-SpeI | CGCACTAGTCTATTCCAGCGGCGGGTCGAAATGGC | Seq ID No: 21 |
| 5'R-PD2-MCS | CCCCAGGCGGCCGCTGTCTAGAGTGGATCCCAGGCCGATGCGTCCGCCGTGCAGGC | Seq ID No: 22 |
| 3'F-PD2-XbaI | ATCTCTAGAATGGGCACCTCGGCCACGCTGGCGCTG | Seq ID No: 23 |
| 3'R-PD2-NotI | AAGTATCGCGGCCGATGAGCGAAACCCTGTTGAAAGTATC | Seq ID No: 24 |
| CmF-BamHI | CGCGGATCCTGATGTCCGGCGGTGCTTTTG | Seq ID No: 25 |
| FHAproF-BamHI | TCTGGATCCCTGCGCTGGCACCCGCGGCGGGCCG | Seq ID No: 26 |
| FHAR-MCS | GCCTCTAGATTCATATGATTCCGACCAGCGAAGTGAAGTAAT | Seq ID No: 27 |
| PRNF-NdeI | CTGGTCGGCATATGAACATGTCTCTGTCACGCATTG | Seq ID No: 28 |
| PRNR-XbaI | GCCTCTAGAGCCTGGAGACTGGCACCGGCCAAGC | Seq ID No: 29 |
| PrnProF-BamHI | CGGGGATCCGCACCCTGGCCTGCGGGCGGGACC | Seq ID No: 30 |
| PRNProR-NdeI | AGACATGTTCATATGGATGCCAGGTGGAGAGCAGA | Seq ID No: 31 |
| 5'F-int | CTAGCGTTCGCATACCAAATCCTTGC | Seq ID No: 32 |
| 5'RCM-int | CCGTAATATCCAGCTGAACGGTCTGG | Seq ID No: 33 |
| 3'FCM-int | TCTGTGATGGCTTCCATGTCGGCAG | Seq ID No: 34 |
| 3'R-int | AGCATGTTGCGGTGTTCCCGGAATG | Seq ID No: 35 |
| 5'FPD-int | ATGACGGAAAGCCGCATGGGCATTGGGTCC | Seq ID No: 36 |
| 3'RPD-int | TTCGTACGTGTTCAGGTGCCGATTGCCGG | Seq ID No: 37 |
| 5'FPD2-int | TGGGCTGGCTGTTCTGGCACGAAACG | Seq ID No: 38 |
| 3'RPD2-int | TTCATCGAATCGGCGCTGATCCTGGC | Seq ID No: 39 |
| PRNF-int | AGGTGCAGCCATACATCAAGGCCAGC | Seq ID No: 40 |

Cloning of S1 Flanking Regions and Insertion of a Chloramphenicol Gene

The chromosomal DNA of *B. pertussis* strain Tohama was used as source material. The upstream region of the S1 gene was amplified by PCR using the 5'F-PT-SalI and 5'R-PT-MCS primers. The latter contains KpnI, XbaI, BglII and NotI sites. The amplification, product was recovered from agarose gel and purified by QIAEX II Extraction kit (Qiagen). The 1287 bp amplification product was digested with SalI and NotI and cloned into the *E. coli* vector pSKΔKpnI digested with the same enzymes. pSKΔKpnI is a derivative of pBluescript II SK+ where the KpnI site has been removed by digestion, fill-in with the Klenow enzyme and re-circularization. The resulting construct was transformed by heat shock into competent cells of *E. coli* DH5α and designated pSK5'. The downstream region was likewise obtained by amplification with the 3'F-PT-XbaI and 3'R-PT-BglII primers. The 1531 bp product was digested with XbaI and BglII and the recovered fragment inserted into pSK5' digested with the same enzymes to obtain pSK53.

Figure 2:
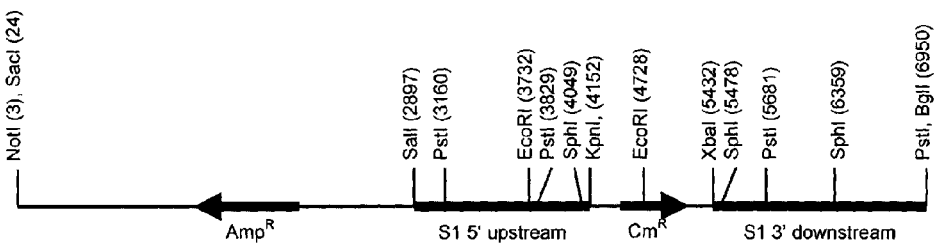
FIG. 2: Vectors for the construction of a modified S1 gene into the allelic exchange vector pSS4245. A: Allelic exchange element for replacing the S1 gene by a chloramphenicol resistance cassette, inserted between the S1 flanking regions. B: Allelic exchange element for returning the modified S1 gene into its exact location in the ptx-ptl operon. To obtain the allelic exchange, these vectors are linearized and inserted into pSS4245, which is then introduced into B. pertussis by conjugative transfer from E. coli SM10.
Figure 2:
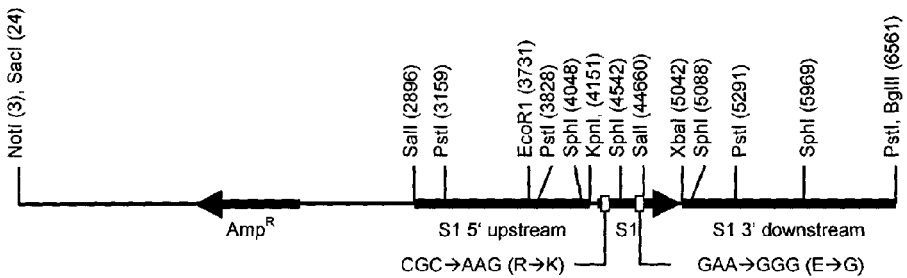

The $Cm^R$ gene was obtained from plasmid pACYC184. The gene was amplified using the primers CmF-KpnI and CmR-XbaI. The 1295 bp PCR product was purified and digested with KpnI and XbaI and inserted into pSK53 cut with the same enzymes. The resulting plasmid was designated pSK5Cm3. This plasmid incorporates the chloramphenicol resistance gene flanked by the 5'-upstream and 3'-downstream regions of the S1 gene (FIG. 2A).

Exchange of the S1 Gene by Homologous Recombination

To perform the allelic exchange into *B. pertussis*, the newly developed vector pSS4245 (FIG. 1) was used. A complete description of this vector has not been published and therefore we report here an overview of its structure. This vector was specifically designed for allelic exchange in *Bordetella* species. It contains a multilinker cloning site where the gene of interest and its flanking sequences on the chromosome can be inserted, several antibiotic resistance genes, including ampicillin used to select the vector and its derivatives in *E. coli*.

The origin of replication is derived from pBR322, which implies that the vector can replicate in *E. coli* but is suicidal in *B. pertussis*. There is also a streptomycin phosphotransferase gene derived from Tn5: this gene is conferring streptomycin resistance to *B. pertussis* but not to *E. coli* [33]. Conjugative transfer between an *E. coli* donor and a *B. pertussis* recipient can happen due to the presence of an origin of transfer derived from plasmid RP4. This requires the use of *E. coli* SM10 as donor strain, providing in trans the necessary conjugative functions derived from RP4 [22]. Conjugation happens merely by streaking together the recipient *B. pertussis* and the donor *E. coli* on agar plates which support the growth of the two bacteria. As the vector is suicidal in *B. pertussis*, streptomycin selects for *B. pertussis* cells which have integrated the whole vector and its $Str^R$ marker by homologous recombination in one of the regions flanking the gene of interest and at the same time eliminates the *E. coli* donor. To resolve this co-integrate and eliminate most of the vector save the gene of interest, pSS4245 incorporates the I-SceI meganuclease gene together with the corresponding cleavage site (FIG. 1) [34]. The nuclease is placed under the control of the ptx-ptl operon promoter. There is no corresponding cleavage site on the *B. pertussis* chromosome. Selection of cointegrates has to be conducted under modulating conditions, where all the virulence factors of *B. pertussis* including PT are repressed. This condition was obtained by adding 20 mM nicotinic acid to the MSS-agar plates used in the mating process. Transfer of the exconjugants mix to MSS-agar without added nicotinic acid relieves the ptx promoter repression and hence the I-SceI nuclease is then expressed. This causes a double strand break in the bacterial chromosome at the level of the nuclease site in the integrated vector. This event is lethal if not repaired. DNA damage also activates the SOS response for repair: the recombination frequency is increased by 2-3 log and the lesion is eventually eliminated by a second homologous recombination [34]. In either case most of the vector is lost. If the second recombination happens in the same flanking region, the original strain is regenerated, if it happens in the other flanking region, the desired strain is obtained. Few colonies need to be screened for their chloramphenicol resistance status as with flanking regions which are of about the same size, the two resulting types of strains, namely parent and recombinant, are about equally distributed.

Plasmid pSK5Cm3 was digested with SacI and BglII and the recovered fragment ligated into pSS4245 cut with SacI and BamHI. After transformation into *E. coli* SM10 the resulting plasmid was designated pSS5Cm3. Fresh cultures of *B. pertussis* strain Tohama (4 days on MSS-agar with 20 mM nicotinic acid) and of *E. coli* SM10 harbouring the vector (overnight on LB-agar with ampicillin, kanamycin and chloramphenicol) were scraped and mixed on agar plates containing LB:MSS (1:1) with 20 mM nicotinic acid and 10 mM MgCl$_2$. After 3 hrs at 35° C., the mix was swabbed onto MSS with 20 mM nicotinic acid, 50 μg/mL streptomycin and 5 μg/mL chloramphenicol. The swab growth was streaked onto MSS-agar with 5 μg/mL chloramphenicol for the second recombination event. The resulting single colonies were tested by replica plating and a few colonies with the $Sm^S$ and $Cm^R$ phenotype were retained for further testing (FIG. 3A). The colonies were confirmed as *B. pertussis* by PCR amplification with *B. pertussis* specific primers. The integration of the $Cm^R$ gene at the designed position was confirmed by PCR with the primers that specifically bind to the upstream 5' (5'F-int and 5'RCM-int primers) and 3' (3'FCM-int and 3'R-int primers) downstream flanking regions and internally in the $Cm^R$ gene. From the PCR analysis, it was confirmed that the 5' and 3' flanking regions were present and that the $Cm^R$ gene had been inserted at the expected location in place of the S1 gene. These verifications also confirmed that the allelic exchange process had not caused any alteration in the S1 flanking regions where recombination had taken place.

Construction of a Modified S1 Gene

The S1 gene was cloned by PCR amplification and mutated by site-directed PCR mutagenesis. The primers S1F-PT-KpnI and S1R-PT-XbaI were used to amplify the gene from chromosomal DNA. The purified PCR product was digested with XbaI and KpnI and the recovered 908 bp fragment was ligated into pSK53 cut with the same enzymes. After transformation and colony selection the resulting plasmid was designated pSK5S13.

Site-directed PCR mutagenesis used the internal F-R9K and R-R9K primers with the sequence mismatch CGC→AAG, causing the R9K substitution. These primers were used in separate reaction cycles. The amplification products were then combined and amplification was continued for 4-5 cycles after annealing. The outer primers were then added to the reaction to generate the entire S1 fragment containing the desired mutation. The same procedure was applied to generate the second mutation using the internal mismatched primers F-E129G and R-E129G, to generate the sequence GAA→GGG, causing the E129G substitution.

The resulting fragment was digested with XbaI and KpnI and inserted into pSK53 cut with the same enzymes to obtain plasmid pSK5S13-9K-129G (FIG. 2B). This was digested with SacI and BglII and the recovered fragment ligated into pSS4245 cut with SacI and BamHI. After transformation into *E. coli* SM10 the resulting plasmid was designated pSS5S13-9K-129G.

Allelic exchange to insert the modified S1 gene back into its original location in the *B. pertussis* chromosome was performed as above but without selection of the exconjugants by chloramphenicol. The desired strains in this case have lost this marker and therefore screening by replica plating was necessary to identify colonies with the desired phenotype $Cm^S$ and $Sm^S$. The resulting Tohama derivative was designated Bp-WWC (FIG. 3B). The integration of the S1 mutated gene at the designed position was confirmed by PCR with the specific primers. The primers could bind the upstream 5' (5'F-int and R-R9K primers) and 3' (F-E129G and 3'R-int primers) downstream flanking regions and inside the S1 gene.

Insertion of a Second Set of the 5 PT Structural Genes

The sequences flanking the targeted insertion site (FIG. 4A) were first cloned to obtain pSKPD5Cm3. The upstream 1688 bp fragment was amplified with the primers 5'F-PD-ApaI and 5'R-PD-MCS, digested with ApaI and KpnI and ligated into pSK5Cm3 cut with the same enzymes to yield pSKPD5'-Cm. The downstream 2980 bp fragment was amplified with the primers 3'F-PD-MCS and 3'R-PD-BglII digested with XbaI and BglII and ligated into pSKPD5'-Cm cut with the same enzymes. The resulting plasmid was designated pSKPD5Cm3 (FIG. 4B).

The conjugative construct was obtained by digesting this plasmid with NotI and Bg/II and ligation into pSS4245 digested with NotI and BamHI. The resulting plasmid was designated pSSPD53-Cm. Conjugative transfer and selection for $Sm^S$ and $Cm^R$ provided the desired *B. pertussis* derivative Bp-PD53-Cm, where the presence of the intact upstream, downstream and $Cm^R$ insert was confirmed by PCR amplification. The primers could bind the upstream 5' (5'FPD-int and 5'RCM-int primers) and 3' (3'FCM-int and 3'RPD-int primers) downstream flanking regions and inside the $Cm^R$ gene.

A functional copy of the ptx operon with its promoter was generated by insertion of the ptx-ptl terminator next to the S3 gene. The five structural genes of PT (modified S1, S2, S4, S5, S3) with its operon promoter were amplified from Bp-WWC DNA using the primers PtxF-BamHI and PtxR-MCS. The 3469 bp amplified product was digested with BamHI and SpeI and the recovered fragment ligated into pSKΔRI cut with the same enzymes to yield pSKptx. pSKΔRI is a variant of pBluescript II SK+ where the EcoRI site has been removed by digestion and fill-in with the Klenow enzyme and re-circularization.

The ptx-ptl operon terminator was then amplified with the TerF-EcoRI and TerR-SpeI primers. The 223 bp product was doubly digested with EcoRI and SpeI and ligated into pSKptx cut with the same enzymes. After transformation and colony selection, the resulting plasmid was designated pSKptxter (FIG. 4C). This plasmid was then doubly digested with BamHI and SpeI and ligated into pSSPD5Cm3 cut with the same enzymes to yield the conjugative vector pSSPDptxter. Allelic exchange into Bp-PD53Cm was performed as described above with replica screening for $Sm^S$ and $Cm^S$ colonies to obtain the strain designated Bp-WWD. The integration of the S1 mutated gene at the designed position was confirmed by PCR with specific primers. The primers could bind the upstream 5' (5'FPD-int and R-R9K primers) and 3' (F-E129G and 3'RPD-int primers) downstream flanking regions and internal S1 gene.

Insertion of a Second Copy of the PRN Structural Gene
Integration of a Chloramphenicol Resistance Gene into the Target Site Selected for Integrating a Second Copy of the PRN Structural Gene.

A derivative of pBluescript SK+ lacking the BamHI site was constructed by digestion with the enzyme, filling-in with the Klenow enzyme and ligation. The resulting plasmid was transformed into E. coli and designated pSKΔH1.

The sequence of the B. pertussis Tohama strain was scanned and pseudo-genes were identified. The DNA sequence between a putative glutathione S-transferase pseudo-gene and a putative aspartate racemase pseudo-gene was selected as the insertion site (posn. 1,344,710-1,345,685 and 1,345,693-1,346049). These genes carry frameshift mutations and are not functional (FIG. 6A).

The 5'-upstream region to the targeted insertion site was amplified using primers carrying SpeI (5'F-PD2-SpeI) and a multilinker including BamHI and NotI (5'R-PD2-MCS) restriction sites. The amplified product was isolated by gel electrophoresis and doubly digested with SpeI and NotI. The resulting fragment was ligated into a fragment of pSKΔH1 digested with the same enzymes. The resulting plasmid was transformed into E. coli and designated pSKPD25. The 3'-downstream fragment was similarly amplified with primers carrying XbaI (3'F-PD2-XbaI) and NotI (3'R-PD2-NotI) restriction sites. After digestion with the same enzymes, the resulting fragment was ligated into a fragment of pSKPD25 digested with the same enzymes. The resulting plasmid was transformed into E. coli and designated pSKPD253.

The chloramphenicol resistance site was obtained by PCR amplification from plasmid pACYC184 using primers carrying a BamHI (CmF-BamHI) and XbaI (CmR-XbaI) restriction site. The PCR product was digested with the two enzymes and cloned into pSKPD253 cut with the same enzymes. After ligation the resulting plasmid was transformed into E. coli, verified by restriction analysis and designated pSKPD25Cm3.

After verification by restriction mapping, the plasmid was digested with NotI and SpeI and the resulting fragment ligated into pSS4245 doubly digested with the same enzymes. The resulting plasmid was designated pSSP2D5Cm3 and transformed into E. coli SM10.

Conjugation was conducted as above, using Bp-WWD as the recipient B. pertussis strain, with selection of $Cm^R$ and $Sm^S$ single colonies. The integration of the $Cm^R$ gene at the designed position was confirmed by PCR with the primers that specifically bind to only the upstream 5' (5'FPD2-int and 5'RCM-int primers) and 3' (3'FCM-int and 3'RPD2-int primers) downstream flanking regions and inside the $Cm^R$ gene.

Integration of Prn Gene Under Control of Fha Promoter

The structural gene of PRN was amplified from B. pertussis DNA using a primer starting at the ATG start codon (F) and a primer carrying an XbaI (R) restriction site. The 2,808 bp amplified product containing only the coding region and the terminator was treated by an 'A' tailing protocol (Promega). The resulting fragment was cloned into the pGEM-T easy vector. The resulting plasmid designated pGEM-TPRN was verified by restriction analysis. In an initial workup to create a second copy of the PRN gene driven by the stronger FHA promoter, the FHA promoter was isolated from B. pertussis DNA by PCR amplification and inserted ahead of the PRN gene. The FHA promoter was amplified by primers carrying the BamHI (FHAproF-BamHI) and a polylinker containing NdeI-XbaI (FHAR-MCS). The purified product was cut with BamHI and XbaI then the recovered DNA fragment was ligated into pSKPD253 also cut with the same enzymes. The resulting plasmid designated pSKPD253Fp was verified by restriction analysis. This plasmid was cut with NdeI and XbaI then ligated with the PCR product of the prn gene which was amplified from pGEMTPRN by PRNF-NdeI and PRNR-XbaI primers and cut with the same enzymes. The resulting plasmid was designated as pSKPD25FpPRN3 (FIG. 6B). The conjugative construct was obtained by digesting this plasmid with NotI and SpeI and ligation into pSS4245 digested with the same enzymes. The resulting plasmid was designated as pSSPD2FpPRN. This construct was inserted at the selected location of the Bp-WWD chromosome to replace the chloramphenicol resistance marker introduced using the usual allelic exchange procedures and screening as described above.

Expression of Prn Gene Under Control of Prn Promoter

The PRN promoter was cloned by PCR amplification of the B. pertussis DNA using primers with the restriction sites BamHI (PrnProF-BamHI) and NdeI (PRNProR-NdeI). The plasmid pSKPD25FpPRN3 was cut with BamHI and NdeI to generate a fragment which had lost the FHA promoter. The PRN promoter was ligated in its place. After transformation into E. coli and verification by restriction analysis, the resulting plasmid was designated pSKPD25PRN3 (FIG. 6C). The plasmid was cut with NotI and inserted into pSS4245 cut with the same enzyme. The resulting construct, pSSPD2prn was transferred into E. coli SM10 to conduct the allelic exchange. The resulting B. pertussis strain was designated Bp-WWE. The integration of prn gene at designed position was confirmed by PCR with the primers that specifically bind to only the upstream 5' (5'FPD2-int and PRNProR-NdeI primers) and 3' (PRNF-int and 3'RPD2-int primers) downstream flanking regions and inside the prn gene.

PT, FHA and PRN Expression in Shaker Flask Culture.

The Bp-WWC, Bp-WWD and Bp-WWE were grown in shake flasks with 100 ml MSS medium supplemented with methylated β-cyclodextrin at 35° C., 200 rpm. After 32-48 hrs of growth, the culture supernatants were collected and assayed by ELISA to quantitate the PT and FHA expression level. PRN expression was determined by western blot densitometric analysis to evaluate also the integrity of the antigen. This assay was conducted both on the clarified culture supernatant and on the cell extract obtained by heating at 60° C. in isotonic buffer.

ELISA Assay for PT and FHA

Purified rabbit polyclonal antibody against PT or FHA (1:1000, NLAC, Thailand) was coated in 96-well plates (NUNC Maxisorp) with 100 μL per well in carbonate/bicarbonate buffer (pH 9.6) and incubated overnight at 4° C. After washing 3 times with phosphate-buffered saline pH 7.4 with 0.1% Tween 20 (PBST), blocking was performed with 100 μl per well of PBST including 3% bovine serum albumin (BSA) then incubated at 37° C. for 1 hr. After discarding the blocking buffer and washing, dilutions of the standard PT, FHA or samples were loaded and incubated at 37° C. for 1 hr. After washing 3 times with PBST, 100 μL of anti-PT subunit S2 mouse monoclonal antibody (1:30,000, Abcam, USA)) or anti-FHA mouse monoclonal antibody (1:10,000, NIBSC, UK) in blocking buffer was added and incubated under the same conditions. After washing the well 3 times with PBST, 100 μL of 1:10,000 dilution in blocking buffer of rabbit anti-mouse (H+L) IgG-HRP conjugate (Abcam, USA) was used as secondary antibody and incubated again for 37° C. for 1 hr. After washing with PST, 100 μL of 3,3',5,5'-tetramethylbenzidine (KPL, USA) were added as the enzyme substrate. The color reaction was terminated with 100 μL of 1 N HCl per well. Optical density was measured at 450 nm using a microtiter plate reader.

Western Blot Assay for PRN

Dilutions of standard PRN and samples were resolved in a 10% SDS-PAGE gel then transferred to a PVDF membrane using a semi-dry blotting system. The membrane was blocked with 5% skimmed milk in PBST for 1 hr. After discarding this blocking solution, the membrane was incubated with 20 mL anti-PRN sheep serum (1:10,000, NIBSC, UK) in blocking buffer for 1 hr, then washed 3 times with PBST. The membrane was then incubated under the same conditions with 20 mL of rabbit anti-sheep IgG-HRP conjugate (Santa Cruz Biotechnology, USA) and washed again. The membranes was then immersed in 3,3'-diaminobenzamidine until the brown color developed. The reaction was terminated by rinsing 2-3 times with deionized water, then left to dry at room temperature. The membrane was scanned and converted to a picture file. PRN concentrations were derived by densitometric analysis of the sample and reference bands using dedicated software.

Genetic Stability

The strains were cultured in 100 ml MSS medium at 35° C. and 200 rpm for 48 hrs, then 0.1 ml of culture was transferred into 100 ml MSS and incubated under the same condition and this step was repeated 4 more times. Each transfer corresponds to 10 generations. The culture was diluted and plated on MSS agar. Thirty isolated colonies were randomly picked. In the selected thirty colonies two were analyzed by PCR to detect the expected presence of the PT and PRN inserts.

CHO Cell Clustering Assay

Chinese hamster ovary (CHO) cell clustering activity was determined by the method of Hewlett et al. [28] In short, CHO cells were cultured in the cRPMI 1640 medium supplemented with 10% fetal bovine serum. The cells were incubated at 37° C. under 5% $CO_2$ atmosphere. The cultured cells were trypsinized and adjusted to $2 \times 10^4$ cells/ml with cRPMI 1640 medium to distribute a 200 μl portion each to wells of a 96-well micro-culture plate. Test samples and reference PT toxin were diluted serially at ten-fold intervals in phosphate buffered saline (PBS) pH 7.4 and a 25 μl volume of the dilutions was added to the wells. After incubation for 48 hr at the same conditions to permit maximal clustering, cells were stained with crystal violet and photographed.

Deposit in Terms of the Budapest Treaty on the International Recognition of the Deposit of Microorganisms for the Purposes of Patent Procedure

| Strain | Deposit Authority | Accession/ Reference Number | Date of Deposit |
|---|---|---|---|
| Bp-WWC | National Institute of Technology and Evaluation, Patent Microorganisms Depositary (NPMD), #122, 2-5-8 Kazusakamatari, Kisarazushi, Chiba 292-0818, Japan | NITE BP-01833 | Mar. 20, 2014 |

REFERENCES

1. Mattoo S, Cherry J D: *Clin Microbiol Rev* 2005, 18:326-382.
2. Aristegui J, Usonis V, Coovadia H, Riedemann S, Win K M, Gatchalian S, Bock H L: Facilitating the WHO expanded program of immunization: the clinical profile of a combined diphtheria, tetanus, pertussis, hepatitis B and *Haemophilus influenzae* type b vaccine. *Int J Infect Dis* 2003, 7:143-151.
3. Miller D L, Ross E M, Alderslade R, Bellman M H, Rawson N S: Pertussis immunisation and serious acute neurological illness in children. *Br Med J* (*Clin Res Ed*) 1981, 282: 1595-1599.
4. Stuart-Harris C: Benefits and risks of immunization against pertussis. *Dev Biol Stand* 1979, 43:75-83.
5. Sato Y, Sato H: Development of acellular pertussis vaccines. *Biologicals* 1999, 27:61-69.
6. Brown B, Greco D, Mastrantonio P, Salmaso S, Wassilak S: Pertussis vaccine trials. Trial synopses. *Dev Biol Stand* 1997, 89:37-47.
7. Monack D, Munoz J J, Peacock M G, Black W J, Falkow S: Expression of pertussis toxin correlates with pathogenesis in *Bordetella* species. *J Infect Dis* 1989, 159:205-210.
8. Weiss A A, Hewlett E L: Virulence factors of *Bordetella pertussis. Ann Rev Microbiol* 1986, 40:661-686.
9. Munoz J J, Arai H, Cole R L: Mouse-protecting and histamine-sensitizing activities of pertussigen and fimbrial hemagglutinin from *Bordetella pertussis. Infect Immun* 1981, 32:243-250.
10. Loosmore S M, Zealey G R, Boux H A, Cockle S A, Radika K, Fahim R E, Zobrist G J, Yacoob R K, Chong P C, Yao F L, et al.: Engineering of genetically detoxified pertussis toxin analogs for development of a recombinant whooping cough vaccine. *Infect Immun* 1990, 58:3653-3662.
11. Nencioni L, Pizza M, Bugnoli M, De Magistris T, Di Tommaso A, Giovannoni F, Manetti R, Marsili I, Matteucci G, Nucci D, et al.: Characterization of genetically inactivated pertussis toxin mutants: candidates for a new vaccine against whooping cough. *Infect Immun* 1990, 58:1308-1315.
12. Pizza M, Covacci A, Bartoloni A, Perugini M, Nencioni L, De Magistris M T, Villa L, Nucci D, Manetti R, Bugnoli M, et al.: Mutants of pertussis toxin suitable for vaccine development. *Science* 1989, 246:497-500.
13. Greco D, Salmaso S, Mastrantonio P, Giuliano M, Tozzi A E, Anemona A, Ciofi degli Atti M L, Giammanco A, Panei P, Blackwelder W C, et al: A controlled trial of two acellular vaccines and one whole-cell vaccine against pertussis. Progetto Pertosse Working Group. *N Engl J Med* 1996, 334:341-348.
14. Makoff A J, Oxer M D, Ballantine S P, Fairweather N F, Charles I G: Protective surface antigen P69 of *Bordetella pertussis*: its characterization and very high level expression in *Escherichia coli*. *Biotechnology (NY)* 1990, 8:1030-1033.
15. Romanos M A, Clare J J, Beesley K M, Rayment F B, Ballantine S P, Makoff A J, Dougan G, Fairweather N F, Charles I G: Recombinant *Bordetella pertussis* pertactin (P69) from the yeast *Pichia pastoris*: high-level production and immunological properties. *Vaccine* 1991, 9:901-906.
16. Nicosia A, Bartoloni A, Perugini M, Rappuoli R: Expression and immunological properties of the five subunits of pertussis toxin. *Inf Immu.* 1987, 55:963-967.
17. Kotob S I, Hausman S Z, Burns D L: Localization of the promoter of the ptl genes of *Bordetella pertussis*, which encode proteins essential for secretion of pertussis toxin. *Infect Immun* 1995, 63:3227-3230.
18. Clare J J, Rayment F B, Ballantine S P, Sreekrishna K, Romanos M A: High-level expression of tetanus toxin fragment C in *Pichia pastoris* strains containing multiple tandem integrations of the gene. *Biotechnology (NY)* 1991, 9:455-460.
19. Rappuoli R: Isolation and characterization of *Corynebacterium diphtheriae* nontandem double lysogens hyperproducing CRM197. *Appl Environ Microbiol* 1983, 46:560-564.
20. Zealey G R, Loosmore S M, Yacoob R K, Cockle S A, Herbert A B, Miller L D, Mackay N J, Klein M H: Construction of *Bordetella pertussis* strains that overproduce genetically inactivated pertussis toxin. *Appl Environ Microbiol* 1992, 58:208-214.
21. Loosmore S M, Yaacoob R K, Zealey G R, Jackson G E D, Yang Y-P, Chong P S-C, Shortreed J M, Coleman D C, Cunningham J D, Gisonni L, Klein M H: Hybrid genes over-express pertactin from *Bordetella pertussis*. *Vaccine* 1995, 13:571-580.
22. Stibitz S: Use of conditionally counterselectable suicide vectors for allelic exchange. *Methods Enzymol* 1994, 235: 458-465.
23. Imaizumi A, Suzuki Y, Ono S, Sato H, Sato Y: Heptakis (2,6-O-dimethyl)b-cyclodetrin: a novel growth stimulant for *Bordetella pertussis* phase I. *J. Clin. Microbiol.* 1983, 17:781-786.
24. Imaizumi A, Suzuki Y, Ono S, Sato H, Sato Y: Effects of heptakis(2,6-O-dimethyl)b-cyclodextrin on the production of pertussis toxin by *Bordetella pertussis*. *Inf. Immun.* 1983, 41:1138-1143.
25. Capiau C, Carr S A, Hemling M E, Plainchamp D, Conrath K, Hauser P, Simoen E, Comberbach M, Roelants P, Desmons P, Permanne P, Petre J O: Purification, characterization, and immunological evaluation of the 69-kDa outer membrane protein of *Bordetella pertussis*. In: *Proceedings of the sixth international symposium on pertussis, Manclark CR (ed., 1990. DHHS publication N° (FDA) 90-1164, pp 7586.
26. Ozcengiz E, Kilinc K, Buyuktanir O, Gunalp A: Rapid purification of pertussis toxin (PT) and filamentous hemagglutinin (FHA) by cation-exchange chromatography. *Vaccine* 2004, 22:1570-1575.
27. Chong P, Jackson G, Cwyk W, Klein M: Simultaneous determination of *Bordetella pertussis* toxin and filamentous haemagglutinin concentrations by hydroxyapatite high-performance liquid chromatography. *J Chromatogr* 1990, 512:227-236.
28. Capiau C, Desmons P: Method for isolating and purifying *Bordetella pertussis* antigenic factors. U.S. Pat. No. 5,391,715.
29. Hewlett E L, Sauer K T, Myers G A, Cowell J L, Guerrant R L: Induction of a novel morphological response in Chinese hamster ovary cells by pertussis toxin. *Infect Immun* 1983, 40:1198-1203.
30. Sauer B: Functional expression of the cre-lox site-specific recombination system in the yeast *Saccharomyces cerevisiae*. *Mol Cell Biol* 1987, 7:2087-2096.
31. Charles I, Fairweather N, Pickard D, Beesley J, Anderson R, Dougan G, Roberts M: Expression of the *Bordetella pertussis* P.69 pertactin adhesin in *Escherichia coli*: fate of the carboxy-terminal domain. *Microbiology* 1994, 140 (Pt 12):3301-3308.
32. Frohlich B T, De Bernardez Cmark E R, Siber G R, Swartz R W: Improved pertussis toxin production by *Bordetella pertussis* through adjusting the growth medium's ionic composition. *J Biotechnol* 1995, 39:205-219.
33. O'Neill E A, Kiely G M, Bender R A: Transposon Tn5 encodes streptomycin resistance in nonenteric bacteria. *J Bacteriol* 1984, 159:388-389.
34. Posfai G, Kolisnychenko V, Bereczki Z, Blattner F R: Markerless gene replacement in *Escherichia coli* stimulated by a double-strand break in the chromosome. *Nucleic Acids Res* 1999, 27:4409-4415.
35. Nicosia et al., Proc. Natl. Acad. Sci. U.S.A. 83, 4631 [1986].
36. Loosmore et al., Nucl. Acids Res. 17, 8365 [1989].
37. Relman et al., Proc. Natl. Acad. Sci. U.S.A. 86, 2637 [1989].
38. Charles et al., Proc. Natl. Acad. Sci. U.S.A. 86, 3554 [1989].
39. Glaser et al., Molec. Microbiol. 2, 19 [1988].
40. Lee et al., 1989, Infect. Immun. 57: 1413-1418.
41. Inatsuka C S, et al., Pertactin is required for *Bordetella* to resist neutrophil-mediated clearance Infect. Immun. 2010, doi:10.1128/IAI.00188-10.
42. Parkhill et al., Comparative analysis of the genome sequences of *Bordetella pertussis, Bordetella parapertussis* and *Bordetella bronchiseptica*. Nature Genetics (2003) 35 32-40.

What is claimed is:

1. A genetically modified *Bordetella pertussis* strain, wherein the Pertussis Toxin S1 gene has Arg9→Lys9 and Glu129→Gly129 mutations, does not include any integrated antibiotic resistance genes and is capable of expressing detoxified Pertussis Toxin (rPT).

2. The modified strain according to claim 1, wherein vector pSS4245 was used to introduce the S1 mutations without integration of an antibiotic resistance gene.

3. The modified strain according to claim 1, which is designated as Bp-WWC and has accession number NITE BP-01833.

4. The modified strain according to claim 1, which is a Tohama strain.

5. The modified strain according to claim 1, which has been further modified by:
(a) integration of at least one copy of the ptx operon into a non-functional region of the chromosome of the modified strain, wherein the integrated ptx operon comprises a set of S2-S5 genes and a S1 gene which has been modified to include the mutations Arg9→Lys9 and Glu129→Gly129, the modified strain thereby having at least two ptx operons which are positioned apart in the chromosome and being capable of expressing enhanced levels of detoxified Pertussis Toxin relative to a strain with only one ptx operon; and/or
(b) integration of at least one copy of a prn gene encoding Pertactin into a non-functional region of the chromosome of the modified strain, the modified strain thereby having at least two prn genes which are positioned apart in the chromosome and being capable of expressing enhanced levels of Pertactin relative to a strain with only one prn gene;
wherein the modified strain does not include any integrated antibiotic resistance genes.

6. The modified strain according to claim 5, wherein vector pSS4245 was used to introduce the copy of the ptx operon and/or prn gene without integration of an antibiotic resistance gene.

7. The modified strain according to claim 5, wherein the copy of the ptx operon and/or prn gene is integrated within or between non functional pseudogenes.

8. The modified strain according to claim 5, which comprises more than one inserted copy of the modified ptx operon and/or more than one inserted copy of the prn gene.

9. The modified strain according to claim 5, which comprises at least two modified ptx operons and/or at least two prn genes.

10. A method of producing the modified *Bordetella pertussis* strain according to claim 1, the method comprising the step of introducing Arg9→Lys9 and Glu129→Gly129 mutations into the S1 gene of a *B. pertussis* strain, thereby resulting in a modified strain being produced which is capable of expressing detoxified Pertussis Toxin (rPT) and which does not include any antibiotic resistance genes.

11. The method according to claim 10, wherein vector pSS4245 is used to introduce the S1 mutations without integration of an antibiotic resistance gene.

12. The method according to claim 10, wherein the *B. pertussis* strain is a Tohama strain.

13. The method according to claim 10, which further comprises the step of:
(a) integrating at least one copy of the ptx operon into a non-functional region of the chromosome of the modified strain, wherein the integrated ptx operon comprises a set of S2-S5 genes and a S1 gene which has been modified to include the mutations Arg9→Lys9 and Glu129→Gly129, thereby producing a modified strain which has at least two ptx operons which are positioned apart in the chromosome and being capable of expressing enhanced levels of detoxified Pertussis Toxin relative to a strain with only one ptx operon; and/or
(b) integrating at least one copy of a prn gene encoding Pertactin into a non-functional region of the chromosome of the modified strain, thereby producing a modified strain which has at least two prn genes which are positioned apart in the chromosome and being capable of expressing enhanced levels of Pertactin relative to a strain with only one prn gene;
wherein the ptx operon and/or prn gene is integrated without integration of any antibiotic resistance gene.

14. The method according to claim 13, wherein vector pSS4245 is used to introduce the copy of the ptx operon and/or prn gene without integration of an antibiotic resistance gene.

15. The method according to claim 13, wherein the ptx operon and/or the prn gene are integrated into or between non functional pseudogenes.

16. The method according to claim 13, wherein a copy of the modified ptx operon and a copy of the prn gene are inserted into the chromosome of the strain.

17. The method according to claim 1, wherein more than one copy of the modified ptx operon is inserted into the chromosome of the strain and/or more than one copy of the prn gene is inserted into the chromosome of the strain.

18. A method of producing *Bordetella pertussis* antigens which comprises the steps of: (i) culturing the genetically modified *B. pertussis* strain of claim 1 in a culture medium to effect expression of the antigens, wherein the antigens include detoxified Pertussis Toxin (rPT), Pertactin and Filamentous Hemagglutinin (FHA) encoded by genes present in the strain; and (ii) recovering the antigens from the culture medium or a cell extract.

* * * * *